(12) United States Patent
Loozen et al.

(10) Patent No.: US 6,780,854 B2
(45) Date of Patent: Aug. 24, 2004

(54) ORALLY ACTIVE ANDROGENS

(75) Inventors: Hubert Jan Jozef Loozen, Uden (NL); Dirk Leysen, Lommel (BE); Jaap van der Louw, Oss (NL)

(73) Assignee: Akzo Nobel NV, Arnhem (NL)

( * ) Notice: Subject to any disclaimer, the term of this patent is extended or adjusted under 35 U.S.C. 154(b) by 0 days.

(21) Appl. No.: 10/280,038

(22) Filed: Oct. 24, 2002

(65) Prior Publication Data

US 2003/0087886 A1 May 8, 2003

Related U.S. Application Data

(62) Division of application No. 09/918,626, filed on Jul. 31, 2001, now Pat. No. 6,541,465, which is a division of application No. 09/613,350, filed on Jul. 11, 2000, now Pat. No. 6,313,108.

(30) Foreign Application Priority Data

Jul. 16, 1999 (EP) .............................. 99202348

(51) Int. Cl.[7] .................... A61K 31/56; C07J 41/00

(52) U.S. Cl. ...................... 514/178; 514/149; 514/182; 206/524.1; 552/575; 552/515; 552/539; 552/632; 552/639; 552/641

(58) Field of Search ................... 514/178, 179, 514/182; 552/575, 515, 632, 639, 641; 206/524.1

(56) References Cited

FOREIGN PATENT DOCUMENTS

GB        1 341 601 A       12/1973

OTHER PUBLICATIONS

Avery et al: "Synthesis and Testing of 17αβ–hydroxy–7α–methyl–D–homoestra–4, 16–dien–3–one: A Highly Potent Orally Action Androgen," Steroids, 1990, vol. 55, No. 2, pp. 59–64.

Solo et al: "7β–Alkyltestosterone Derivatives: Synthesis and Activity as Androgens and as Aromatase Inhibitors," Steroids, 1982, vol. 40, No. 6, pp. 603–614.

*Primary Examiner*—Sabiha Qazi
(74) *Attorney, Agent, or Firm*—William P. Ramey, III

(57) ABSTRACT

Novel, orally active androgens are 7α-substituted $\Delta^{14}$-nandrolone derivatives. The compounds satisfy the general formula:

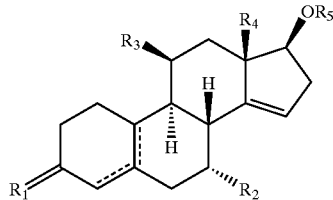

Formula I wherein
$R_1$ is O, (H,H), (H,OR), NOR, with R being hydrogen, $(C_{1-6})$ alkyl, or $(C_{,1-6})$ acyl;
$R_2$ is selected from the group consisting of $(C_{2-4})$ alkyl, $(C_{2-4})$ alkenyl, or $(C_{2-4})$ alkynyl, each optionally substituted by halogen; or
$R_2$ is cyclopropyl, or cyclopropenyl, each optionally substituted by $(C_{1-2})$ alkyl, or halogen;
$R_3$ is hydrogen, $(C_{1-2})$ alkyl, or ethenyl;
$R_4$ is $(C_{1-2})$ alkyl;
$R_5$ is hydrogen, or $(C_{1-15})$ acyl;
and the dotted lines indicate optional bonds.

3 Claims, No Drawings

ORALLY ACTIVE ANDROGENS

This application is a divisional of U.S. application Ser. No. 09/918,626, filed on Jul. 31, 2001 now U.S. Pat. No. 6,541,465, which is a divisional of U.S. application Ser. No. 09/613,350, filed on Jul. 11, 2000 now U.S. Pat. No. 6,313,108.

The invention is in the field of orally active androgenic hormones, more specifically $\Delta^{14}$ derivatives of 19-nortestosterone.

Testosterone derivatives are known. As a medicine testosterone itself, the natural male hormone, has many known drawbacks as far as methods of administration are concerned. It has a short-lasting activity, is insoluble in the usual pharmaceutically acceptable media, and is not very potent. The more potent dihydrotestosterone (5α-reduced form of testosterone) is considered a health-risk, notably for the prostate.

A more potent androgen is 7α-methyl-19-nortestosterone (MENT) disclosed in FR 4,521 M and U.S. Pat. No. 5,342,834. An important drawback of MENT, however, is its unfavourable kinetics which limits its use as an orally active androgen.

In the field of pharmaceutical preparations in general it is a common desire for a medicinal agent to be orally active. Oral dosage forms, e.g. solid dosage forms such as tablets and capsules, are among the most widely accepted forms of administration. In the field of androgens, a particular desire exists for the oral administration in connection with a utility such as male contraception. Since in the area of female contraception the word "pill" has almost become a synonym for reliable birth-control, it is evident that also in the case of male contraception oral activity is desired, so as to enable providing a male "pill."

An androgen having a special position in the field, is the so-called "Segaloff steroid" which is a 19-nortestosterone derivative having, as in MENT, a 7α-methyl group, and which has a double bond between carbon atoms 14 and 15 ($\Delta^{14}$). This special position is due to the fact that it has long been recognized as the most potent oral androgen known. See, int.al. Avery et al, *Steroids*, 55, 59 (1990). The compound, together with its 7α-H analogue, is also known from GB 1,341,601.

Despite having a special position in the field, the "Segaloff steroid" has not found practical use, which may be due to several drawbacks it has for clinical utility. E.g., with 19-nortestosterones metabolic stability is an issue. Thus it is known from GB 1,341,601 that these compounds are prone to metabolic inactivation by hepatic 17β-hydroxysteroid dehydrogenase. The classic solution to this problem, the introduction of an alkyl group in the 17α position is believed to be responsible for unsatisfactory results such as a limited activity.

Several, mostly very old publications can be mentioned which form the further background-art relating to groups of steroid compounds which include 19-nortestosterone derivatives. None of these references teaches orally active androgens.

Thus, in FR 1,432,561, published in 1966, 19-nortestosterones like MENT having an alkyl substituent at C-7 are employed as a starting material for hormonal agents having a double bond between carbon atoms 5 and 6. Alkyl groups other than methyl are not disclosed.

BE 861 224 concerns all possible esters of a wide variety of 17-hydroxysteroids. The disclosure, which dates from 1976, specifically teaches that certain esters are desired for prolonged activity of the steroids. Among the large group of steroids disclosed are oestrogens, anti-oestrogens, androgens and anabolics. A great many possible substituents at various positions is given, among which are methyl and ethyl at C-7.

Chemical Abstracts 110: 95601y (1989) refers to a 17-hydroxy acetate of 7-allyl-19-nortestosterone as an intermediate in the synthesis of 7-allyloestradiol.

EP 159 739 teaches immunomodulating agents of the oestrane series, including particularly $\Delta^{4}$- and $\Delta^{5(10)}$-oestrene derivatives having an alkyl substituent in position 6 or 7. Said alkyl substituent typically is methyl.

DE 20 43 404 concerns 7β-steroids which have anti-hormonal activities. The alkyl substituent mostly is methyl, but ethyl and propyl are disclosed as well. In the synthesis of 7β-ethyl-19-nortestosterone, which is a compound according to the teaching of DE 20 43 404, the 7α-isomer is formed as well. It is not taught to use this isomer for anything, and the teaching of this document does not distinguish the ethyl or propyl substituents from the methyl moiety.

As background art reference is further made to Solo et al, *Steroids*, 40, 603–614 (1990). Disclosed herein are various 7α-alkyl derivatives of testosterone.

It is an object of the invention to provide orally active androgens which are an improvement as compared to the Segaloff steroid in that they are better suitable for clinical use, and particularly possess sufficient oral activity and metabolic stability.

According to the invention, compounds are provided satisfying the general formula I given below.

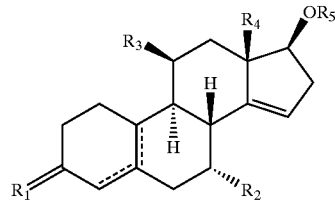

Formula I wherein
R$_1$ is O, (H,H), (H,OR), NOR, with R being hydrogen, (C$_{1-6}$) alkyl, or (C$_{1-6}$) acyl;
R$_2$ is selected from the group consisting of (C$_{2-4}$) alkyl, (C$_{2-4}$) alkenyl, or (C$_{2-4}$) alkynyl, each optionally substituted by halogen; or
R$_2$ is cyclopropyl, or cyclopropenyl, each optionally substituted by (C$_{1-2}$) alkyl, or halogen;
R$_3$ is hydrogen, (C$_{1-2}$) alkyl, or ethenyl;
R$_4$ is (C$_{1-2}$) alkyl;
R$_5$ is hydrogen, or (C$_{1-15}$) acyl;
and the dotted lines indicate optional bonds.

The invention includes pharmaceutically acceptable salts or esters, prodrugs and precursors of the above steroids.

The term (C$_{1-6}$) alkyl as used in the definition of formula I means a branched or unbranched alkyl group having 1–6 carbon atoms, like methyl, ethyl, propyl, isopropyl, butyl, isobutyl, tertiary butyl, pentyl, and hexyl. Likewise, the term (C$_{2-4}$) alkyl means a branched or unbranched alkyl group having 2–4 carbon atoms and the term (C$_{1-2}$) alkyl means an alkyl group having 1–2 carbon atoms.

The term (C$_{2-4}$) alkenyl means a branched or unbranched alkenyl group having at least one double bond and 2–4 carbon atoms. Preferred alkenyl groups have 2–3 carbon atoms, such as vinyl and propenyl.

The term (C$_{2-4}$) alkynyl means a branched or unbranched alkynyl group having at least one triple bond and 2–4 carbon atoms. Preferred alkynyl groups have 2–3 carbon atoms, such as ethynyl and propynyl.

The term (C$_{1-6}$) acyl means an acyl group derived from a carboxylic acid having 1–6 carbon atoms, like formyl, acetyl, propanoyl, butyryl, 2-methylpropanoyl, pentanoyl, pivaloyl, and hexanoyl. Likewise, the term (C$_{1-15}$) acyl means an acyl group derived from a carboxylic acid having 1–15 carbon atoms. Also included within the definition of (C$_{1-6}$) acyl or (C$_{1-15}$) acyl are acyl groups derived from dicarboxylic acids, like hemi-maloyl, hemi-succinoyl, hemi-glutaroyl, and so on. Preferred is hemi-succinoyl.

The term halogen means fluorine, chlorine, bromine, or iodine. When halogen is a substituent at an alkyl group, Cl and F are preferred, F being most preferred.

It is understood that the 7α-substituted Δ$^{14}$-nandrolone derivatives of the invention have the natural configurations 5α, 8β, 9α, 10β, 13β and 17β.

The 7α-substituted Δ$^{14}$-nandrolone derivatives of this invention have the natural configurations 5α, 8β, 9α, 10β, 13β and 17β, and may possess also one or more additional chiral carbon atoms. The compounds may therefore be obtained as a pure diastereomer, or as a mixture of diastereomers. Methods for obtaining the pure diastereomers are well known in the art, e.g. crystallization or chromatography.

The compounds of the invention, which are distinguished from the aforementioned known "Segaloff steroid" by the length of the 7α substituent, surprisingly are an improvement over said known steroid and have unexpected advantages for clinical utility. This is exhibited by, inter alia, a surprisingly better oral activity. Preferred compounds of the invention further display a much better metabolic stability than the Segaloff steroid.

Preferred compounds of the invention have R$_2$ selected from the group consisting of ethyl, ethenyl, ethynyl, propyl, 1-propenyl, 2-propenyl, 1-propynyl, 1,2-propadienyl, and cyclopropyl.

Even more preferred are compounds in which R$_1$ is oxo, R$_3$ is hydrogen, R$_4$ is methyl, and the dotted lines indicate a Δ$^4$ double bond.

Most preferred are those compounds in which R$_2$ is C$_2$, with the highest preference being ethyl or ethenyl.

The compounds of the invention may be produced by various methods known in the art of organic chemistry in general, and especially in the art of the chemistry of steroids (see, for example: Fried, J. et al, *Organic Reactions in Steroid Chemistry*, Volumes I and II, Van Nostrand Reinhold Company, New York, 1972).

Essential is the introduction of a saturated or unsaturated 7α-substituent (optionally substituted by halogen) onto the steroid nucleus, and the introduction of a Δ$^{14}$ double bond. A convenient starting material for the preparation of compounds of formula I wherein R$_1$ is oxo, R$_2$, R$_3$ and R$_4$ have the previously given meaning, R$_5$ is hydrogen, and the dotted lines indicate a Δ$^4$ double bond, is for instance a gon-4-en-3-one derivative of general formula II, wherein R$_3$ and R$_4$ have the previously given meaning, and R$_6$ is oxo, (17α-H,17β-OR$_7$), or (17α-C≡CH,17β-OR$_7$), in which R$_7$ is a hydroxy protecting group, such as an acyl group, like an acetyl group, a benzoyl group or a pivaloyl group, an alkoxyalkyl group, like an ethoxyethyl group or a tetrahydropyranyl (THP) group, or a silyl group, such as a trimethylsilyl group or a tert-butyldimethylsilyl group, whose synthesis is known in literature, or which can be prepared using standard methods.

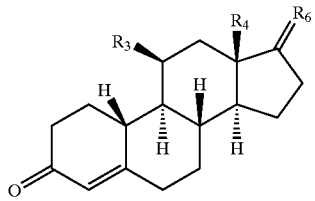

Formula II

A possible synthesis route is as follows. A gon-4-en-3-one derivative of formula II can be converted to the the corresponding gona-4,6-dien-3-one derivative by using standard methods, e.g. by conversion to the 3-acyloxy- or 3-alkoxygona-3,5-diene derivative followed by reaction with 2,3,5,6-tetrachloro-1,4-benzoquinone [Solyom, S. et al, Steroids 35, 361 (1980)]. Then, the 7α-substituent, or a precursor thereof, is introduced by conjugate addition (1,6-addition). For this reaction several methodologies are known in the art, among others:

1)—Conjugate addition of organocopper reagents [for conjugate additions of organocopper reagents, see Lipshutz, B. H. et al in Org. Reactions 41, p. 135, Wiley, New York, 1992].

2)—Transition metal-mediated (TiCl$_4$, AlCl$_3$, ZrCl$_4$, etc.) reaction of an organosilicon compound [formal 1,6-addition; see e.g. Nickisch, K. et al, Tetrahedron Lett. 29, 1533 (1988)].

3)—Base-catalyzed conjugate addition of a dialkyl malonate, 2,2-dimethyl-1,3-dioxane-4,6-dione, or an alkyl cyanoacetate [see e.g. Cruz, R. et al, Austr. J. Chem. 35, 451 (1982)].

4)—Conjugate addition of a suitable cyanide (MC≡N, M is Li, Na, K, AlR$_2$, SiR$_3$ etc.). In general, these methods result in the predominant or exclusive formation of the 7α-isomer.

The 7α-substituted gon-4-en-3-one thus obtained can be aromatized to the 3-hydroxygona-1,3,5(10)-triene [Yuan, S.-S. et al, Steroids 39, 279 (1982)] which then can be methylated to the 3-methoxy derivative. Conversion to a 3-methoxygona-1,3,5(10)-triene can also be achieved directly [Brito, M. et al, Synth. Commun. 26, 623 (1996)]. When R$_6$ is (17α-H,17β-OR$_7$), the 17-hydroxy group is deprotected and oxidized to produce a 3-methoxygona-1,3,5(10)-trien-17-one derivative [for oxidation reactions, see: Hudlicky, M., *Oxidations in Organic Chemistry*, ACS Monograph 186, Washington, D.C., 1990]. When R$_6$ is (17α-C≡CH,17β-OR$_7$), the 17-hydroxy group is again deprotected and the 17α-ethynyl-17β-hydroxy derivative is converted to the 17-ketone e.g. by reaction with silver carbonate on celite [Rao, P. N. et al, Steroids 59, 621 (1994)] or other methods known in the art. In both cases, conversion to the 17-ketone can also be accomplished prior to aromatization. The 3-methoxygona-1,3,5(10)-trien-17-one derivative thus obtained can be brominated directly, for instance by reaction with copper(II) bromide in benzene/methanol [Segaloff, A. et al, Steroids 22, 99 (1973)]. The 3-methoxygona-1,3,5(10)-trien-17-one derivative can also be converted to the enol acetate and then treated with bromine [Johnson, W. S. et al, J. Am. Chem. Soc. 79, 2005 (1957)], or to the enol silyl ether followed by reaction with e.g. N-bromosuccinimide [Heathcock, C. H. et al, J. Amer. Chem. Soc. 104, 6081 (1982)]. Dehydrobromination of the 16α-bromoketone, e.g. by reaction with LiBr/Li$_2$CO$_3$/DMF [Bull, J. R. et al, J. Chem. Soc., Perkin Trans. I, 241 (1990)], usually results in a mixture of (14β)-3-methoxygona-1,3,5(10),15-tetraen-17-one and 3-methoxygona-1,3,5(10),14- tetraen-7-one derivatives. They can be separated whereafter the latter is reduced to the corresponding (17β)-3-methoxygona-1,3,5(10),14-tetraen-17-ol derivative by use of sodium borohydride, lithium aluminium hydride or other reducing agents.

The 7α-substituted 3-methoxygona-1,3,5(10)-trien-17-one derivative can also be converted to the corresponding cyclic 1,2-ethanediyl acetal which is then brominated to afford a (16α)-16-bromo-3-methoxygona-1,3,5(10)-trien-17-one cyclic 1,2-ethanediyl acetal derivative. Bromination can be accomplished using pyridinium tribromide, phenyltrimethylammonium tribromide or other brominating agents known in the art [Rasmusson, G. H. et al, Steroids 22, 107 (1973)]. The 16α-bromo compound is dehydrobrominated by reaction with a base, e.g. potassium tert-butoxide in xylene or dimethyl sulfoxide, to give the $\Delta^{15}$ compound [Johnson, supra; Poirier, D. et al, Tetrahedron 47, 7751 (1991)]. Mild hydrolysis of the ethylene ketal, for instance by treatment with p-toluenesulfonic acid in a mixture of acetone and water [Johnson, supra], results in a 3-methoxygona-1,3,5(10),15-tetraen-17-one derivative which is then converted to a 3-methoxygona-1,3,5(10),14,16-pentaen-17-ol acetate by acid-catalyzed reaction with acetic anhydride, isopropenyl acetate or other acetylating agents [Rasmusson, supra; Bull, supra]. The acetate is treated with sodium borohydride or other reducing agents [Rasmusson, supra] to result in the formation of a (17β)-3-methoxygona-1,3,5(10),14-tetraen-17-ol derivative. Optionally, a 3-methoxygona-1,3,5(10),15-tetraen-17-one cyclic 1,2-ethanediyl acetal can be converted by acid-catalyzed isomerization into the corresponding $\Delta^{14}$ derivative [Ponsold, K. et al, J. Prakt. Chem. 323, 819 (1981)]. Removal of the acetal and reduction of 17-oxo produces the (17β)-3-methoxygona-1,3,5(10),14-tetraen-17-ol derivative. A 3-methoxygona-1,3,5(10),15-tetraen-17-one can also undergo isomerization to give a mixture of (14β)-3-methoxygona-1,3,5(10),15-tetraen-17-one and 3-methoxygona-1,3,5(10),14-tetraen-17-one derivatives which can be processed as described above.

Additional methods to introduce a $\Delta^{15}$ double bond include: conversion of a 3-methoxygona-1,3,5(10)-trien-17-one derivative to the enol acetate and reaction with a palladium(II) salt [Takahashi, T. et al, Tetrahedron 41, 5747 (1985)], or reaction of the enolate with methyl 2-pyridinesulfinate [Dionne, P. et al, Steroids 62, 674 (1997)].

Birch reduction of the 7α-substituted (17β)-3-methoxygona-1,3,5(10),14-tetraen-17-ol derivative thus obtained [Caine, D. in Org. Reactions 23, p. 1, Wiley, New York, 1976] and hydrolysis of the resulting (17β)-3-methoxygona-2,5(10),14-trien-17-ol derivative then provides a 7α-substituted (17β)-17-hydroxygona-4,14-dien-3-one derivative of the invention. In cases where the 7α-substituent is constructed from a precursor thereof (i.e. an unsaturated 7α-substituent, a malonic ester fragment, or a cyano group, see above), this operation, which can be accomplished using standard methods, often must take place simultaneously with the introduction of the $\Delta^{14}$ double bond. The precise sequence of reaction steps needed for construction of the 7α-substituent and for the introduction of the $\Delta^{14}$ double bond, including the Birch reduction and the conversion of the resulting gona-2,5(10)-diene to the 7α-substituted (17β)-17-hydroxygona-4,14-dien-3-one derivative of the invention is dictated by methods common in synthetic strategy (see Example 4 and 5).

Compounds of the invention in which $R_1$ is (H,H), (H,OR), NOR, with R being hydrogen, $(C_{1-6})$ alkyl, $(C_{1-6})$ acyl, are obtained, by using methods known in the art, from compounds of formula I in which $R_1$ is oxo.

Compounds of the invention in which $R_5$ is $(C_{1-15})$ acyl are obtained, by using methods known in the art, from compounds of formula I in which $R_5$ is hydrogen.

Compounds of the invention in which the dotted lines indicate a $\Delta^{5(10)}$ double bond are produced from the $\Delta^{2,5(10)}$ dienes obtained after the Birch reduction. Alternatively, they can be prepared from $\Delta^4$ derivatives by isomerization. 5α-Reduced compounds of the invention are produced from $\Delta^4$ derivatives.

The invention will be further explained hereinafter with reference to the following Examples.

EXAMPLE 1

(7α,17β)-7-Ethyl-17-hydroxyestra-4,14-dien-3-one (a) and (7α, 17β)-7-ethyl-17-hydroxyestra-5(10),14-dien-3-one (b)

i)—Chlorotrimethylsilane (19 ml) was added in 5 min. to a suspension of (17α)-17-hydroxy-19-norpregna-4,6-dien-20-yn-3-one [Syntex S.A., GB 935116 (1958); 18.0 g] in a mixture of dichloromethane (300 ml) and pyridine (25 ml), cooled to 0° C. After 2 h stirring at 0° C. the reaction mixture was poured into a saturated aqueous solution of sodium hydrogencarbonate. The product was extracted into dichloromethane; the combined organic phases were washed with water and brine, dried over sodium sulfate and concentrated under reduced pressure, to afford (17α)-17-[(trimethylsilyl)oxy]-19-norpregna-4,6-dien-20-yn-3-one (22.3 g). The product was used in the following step without further purification.

ii)—A mixture of lithium (5.0 g) and dry diethyl ether (200 ml) was cooled to −30° C. Bromoethane (26.9 ml) was added dropwise whereafter the resulting solution of ethyllithium was transferred to a suspension of copper(I) iodide (30.6 g) in dry tetrahydrofuran (140 ml), cooled to −30° C. The resulting cuprate solution was stirred for 45 min. at that temperature and a solution of the product obtained in the previous step (20.0 g) in dry tetrahydrofuran (160 ml) was added dropwise. After 45 min. stirring at −25° C., chlorotrimethylsilane (20 ml) was added and stirring was continued for another 30 min. The reaction mixture was poured into a saturated aqueous solution of ammonium chloride and the product was extracted into ethyl acetate. The combined organic phases were washed with a saturated aqueous solution of ammonium chloride and brine, dried over sodium sulfate and concentrated under reduced pressure, to give (7α,17α)-7-ethyl-3,17-bis[(trimethylsilyl)oxy]-19-norpregna-3,5-dien-20-yne (29.5 g). The product was used in the following step without further purification.

iii)—A solution of the product obtained in the previous step (29.5 g) in acetone (400 ml) was treated with hydrochloric acid (2.3 M, 20 ml). After 1.5 h stirring at room temperature, the reaction mixture was neutralized with a saturated aqueous solution of sodium hydrogencarbonate. The acetone was removed under reduced pressure and the product was extracted into ethyl acetate. The combined organic phases were washed with brine, dried over sodium sulfate and concentrated under reduced pressure, to give (7α,17α)-7-ethyl-17-hydroxy-19-norpregn-4-en-20-yn-3-one (19.5 g). The product was used in the following step without further purification.

iv)—Hydrochloric acid (6 M, 240 ml) was added dropwise to a suspension of dicalite (240 g) in methanol (1200 ml). After 20 min. stirring at room temperature the dicalite was collected by filtration and washed with water until neutral. Then, it was suspended in water (960 ml). With vigorous stirring, copper(II) nitrate trihydrate (145 g) was added, followed by careful addition of a solution of sodium carbonate (72.2 g) in water (360 ml). After 30 min. stirring, the product was collected by filtration and washed with water until neutral. The product was dried at 80° C. under reduced pressure, to give copper(II) carbonate on dicalite (310 g). A mixture of the product obtained under iii (19.5 g) and copper(II) carbonate on dicalite (70 g) in toluene (330 ml) was heated at reflux temperature for 9 h under removal of water by use of a Dean-Stark trap. The reaction mixture was filtered, the residue thoroughly washed with ethyl acetate, and the filtrate was concentrated under reduced pressure. Column chromatography gave (7α)-7-ethylestr-4-ene-3,17-dione (9.14 g).

v)—A solution of the product obtained in the previous step (9.14 g), copper(II) bromide (13.6 g), and lithium bromide (2.64 g) in acetonitrile (285 ml) was stirred at room temperature for 4 h. The reaction mixture was poured into water and the product extracted into ethyl acetate. The combined organic phases were was washed with a saturated aqueous solution of ammonium chloride and brine, dried over sodium sulfate and concentrated under reduced pressure. Column chromatography afforded (7α)-7-ethyl-3-hydroxyestra-1,3,5(10)-trien-17-one (6.54 g).

vi)—A mixture of the product obtained in the previous step (6.54 g), dry potassium carbonate (18.6 g), iodomethane (5.6 ml), and dry dimethylformamide (22 ml) was stirred at room temperature for 3.5 h. The reaction mixture was poured into water and the product extracted into ethyl acetate. The combined organic phases were washed with water, a saturated aqueous solution of ammonium chloride and brine, dried over sodium sulfate and concentrated under reduced pressure, to give (7α)-7-ethyl-3-methoxyestra-1,3,5(10)-trien-17-one (6.77 g). The product was used in the following step without further purification.

vii)—A solution of diisopropylamine (6.15 ml) in dry tetrahydrofuran (70 ml) was cooled to −30° C. n-BuLi (1.6 M solution in hexanes, 27.5 ml) was added dropwise and stirring was continued for 30 min. The reaction mixture was cooled to −50° C. and a solution of the product obtained in the previous step (6.95 g) in dry tetrahydrofuran (100 ml) was added dropwise. Stirring was continued for 1 h. After cooling to −60° C., chlorotrimetlhylsilane (11.1 ml) was added. The mixture was stirred for 20 min. and then treated with a solution of phenyltrimethylammonium tribromide (10.0 g) in dry pyridine (31 ml). After 1 h stirring at −60° C., the mixture was poured into water and the product was extracted into ethyl acetate. The combined organic phases were washed with a saturated aqueous solution of sodium hydrogencarbonate and brine, dried over sodium sulfate and concentrated under reduced pressure. Column chromatography afforded (7α,16α)-16-bromo-7-ethyl-3-methoxyestra-1,3,5(10)-trien-17-one (8.75 g).

viii)—A mixture of the product obtained in the previous step (8.75 g), lithium bromide (12.7 g) and lithium carbonate (10.9 g) in dry dimethylformamide (77 ml) was heated under reflux for 3.25 h. After cooling, the reaction mixture was poured into water and the product was extracted into ethyl acetate. The combined organic phases were washed with water and brine, dried over sodium sulfate and concentrated under reduced pressure. Column chromatography afforded (7α)-7-ethyl-3-methoxyestra-1,3,5(10),14-tetraen-17-one (4.31 g) and (7α,14β)-7-ethyl-3-methoxyestra-1,3,5(10),15-tetraen-17-one (1.0 g).

ix)—A solution of sodium borohydride (0.21 g) and sodium hydroxide (0.44 g) in methanol (50 ml) was added dropwise to a solution of (7α)-7-ethyl-3-methoxyestra-1,3,5(10),14-tetraen-17-one (4.31 g) in dichloromethane (12 ml) and methanol (20 ml), cooled to 0° C. The reaction mixture was stirred for 1.5 h, quenched with acetone (4 ml), and then poured into a saturated aqueous solution of ammonium chloride. The product was extracted into ethyl acetate; the combined organic phases were washed with brine, dried over sodium sulfate and concentrated under reduced pressure, to give (7α,17β)-7-ethyl-3-methoxyestra-1,3,5(10),14-tetraen-17-ol (4.28 g). The product was used in the following step without further purification.

x)—The alcohol obtained in the previous step (1.5 g) in dry tetrahydrofuran (24 ml) was added to a refluxing solution of lithium (2.12 g) in liquid ammonia (98 ml). After 4.5 h stirring at −35° C., 2-propanol was added in 30 min. and the ammonia was allowed to evaporate. Water was added and the product was extracted into ethyl acetate. The combined organic phases were washed with brine, dried over sodium sulfate and concentrated under reduced pressure, to give (7α,17β)-7-ethyl-3-methoxyestra-2,5(10),14-trien-17-ol (1.65 g). The product was used in the following step without further purification.

xi)—A mixture of silica (5.2 g), a saturated aqueous solution of oxalic acid (0.52 ml) and dichloromethane (14 ml) was stirred at room temperature for 10 min. A solution of the product obtained in the previous step (1.6 g) in dichloromethane (5 ml) was added and stirring was continued for 1.5 h. Solid sodium hydrogencarbonate was added and stirring was continued for 10 min. The mixture was filtered and the filtrate was concentrated under reduced pressure. Column chromatography of the crude product afforded (7α,17D)-7-ethyl-17-hydroxyestra-5(10),14-dien-3-one (1.03 g), $^1$H-NMR (CDCl$_3$)δ5.04 (bs, 1H), 4.03 (t, 1H, J=8.4 Hz), 2.76 (bs, 2H), 0.98 (s, 3H), 0.93 (t, 3H, J=6.6 Hz).

xii)—Following a procedure analogous to that described under iii, the product obtained in the previous step (0.45 g) was converted to (7α,17β)-7-ethyl-17-hydroxyestra-4,14-dien-3-one (0.24 g), m.p. 102–105° C.

EXAMPLE 2

(7α,17β)-7-Ethenyl-17-hydroxyestra-4,14-dien-3-one i)—A solution of (17β)-17-(acetyloxy)estra-4,6-dien-3-one [Syntex, DE 1143199 (1963); 50.0 g], lithium thiophenoxide (1.0 M solution in tetrahydrofuran, 16 ml), copper (I) bromide-dimethyl sulfide complex (3.18 g) and lithium bromide (1.38 g) in dry tetrahydrofuran (167 ml) was cooled to −15° C. Vinylmagnesium chloride (2 M solution in tetrahydrofuran, 159 ml) was added dropwise (T≦−15° C.) and stirring was continued for 30 min. A saturated aqueous solution of ammonium chloride was added dropwise and stirring was continued for another 15 min. The reaction mixture was filtered over dicalite and the product was extracted into ethyl acetate. The combined organic phases were concentrated under reduced pressure and the residue was dissolved into acetone (1000 ml). Hydrochloric acid (4 M, 100 ml) was added and the mixture was stirred for 30 min. at room temperature. A saturated aqueous solution of sodium hydrogencarbonate was added and the acetone was removed under reduced pressure. The product was extracted into ethyl acetate; the combined organic phases were washed with brine, dried over sodium sulfate and concentrated under reduced pressure, to give a mixture of (7α,17β)-17-(acetyloxy)-7-ethenylestr-4-en-3-one and (7β,17β)-17-(acetyloxy)-7-ethenylestr-4-en-3-one (57.3 g, ratio 85:15). The product was used in the following step without further purification.

ii)—Potassium hydroxide (26.7 g) was added in portions to a solution of the product obtained in the previous step (57.3 g) in tetrahydrofuran (833 ml), methanol (738 ml), and water (238 ml). The reaction mixture was stirred for 45 min. at room temperature and then neutralized with concentrated hydrochloric acid (20 ml). The tetrahydrofuran and methanol were partially removed under reduced pressure and the product was extracted into ethyl acetate. The combined organic phases were washed with water and brine, dried over sodium sulfate and concentrated under reduced pressure. Column chromatography afforded (7α,17β)-7-ethenyl-17-hydroxyestr-4-en-3-one (36.7 g).

iii)—A mixture of the product obtained in the previous step (66.2 g), trimethyl orthoformate (80 ml), copper(II) bromide (65.2 g), and methanol (1788 ml) was heated under reflux for 50 min. After cooling, the reaction mixture was filtered. The filtrate was concentrated under reduced pressure and the residu dissolved in ethyl acetate. The ethyl acetate solution was washed with a saturated aqueous solution of sodium hydrogencarbonate and brine, dried over sodium sulfate and concentrated under reduced pressure. Column chromatography afforded (7α,17,β)-7-ethenyl-3-methoxyestra-1,3,5(10)-trien-17-ol (42.9 g).

iv)—Tetrapropylammonium perruthenate (2.76 g) was added to a solution of the product obtained in the previous step (41.1 g) and 4-methylmorpholine N-oxide (46.2 g) in acetone (1080 ml). After 1 h stirring at room temperature the reaction mixture was filtered over dicalite and silica. The filtrate was concentrated under reduced pressure. Column chromatography afforded (7α)-7-ethenyl-3-methoxyestra-1,3,5(10)-trien-17-one (38.1 g).

v)—p-Toluenesulfonic acid (3.21 g) was added to a solution of the product obtained in the previous step (36.05 g) in a mixture of ethylene glycol (108 ml) and triethyl orthoformate (188 ml). The reaction mixture was stirred at room temperature for 2 h. Water (1800 ml) was added and stirring was continued for 1 h. The product was extracted into ethyl acetate; the combined organic phases were washed with a saturated aqueous solution of sodium hydrogencarbonate and brine, dried over sodium sulfate, and concentrated under reduced pressure, to give (7α)-7-ethenyl-3-methoxyestra-1,3,5(10)-trien-17-one cyclic 1,2-ethanediyl acetal (41.37 g). The product was used in the following step without further purification.

vi)—Phenyltrimethylammonium tribromide (22.60 g) was added in portions to a solution of the product obtained in the previous step (21.37 g) in dry tetrahydrofuran (114 ml). The reaction mixture was stirred for 40 min., and then treated with additional portions of phenyltrimethylammonium tribromide until the reaction was complete. After 30 min. stirring the mixture was poured into an aqueous solution of sodium thiosulfate (10%) and the product was extracted into ethyl acetate. The combined organic phases were washed with a saturated aqueous solution of sodium hydrogencarbonate and brine, dried over sodium sulfate and concentrated under reduced pressure, to give (7α, 16α)-16-bromo-7-ethenyl-3-methoxyestra-1,3,5(10)-trien-17-one cyclic 1,2-ethanediyl acetal (34.91 g). The product was used in the following step without further purification.

vii)—A solution of the product obtained in the previous step (34.91 g) in dry dimethyl sulfoxide (178 ml) was treated with potassium tert-butoxide (13.5 g) and the reaction mixture was stirred at 40° C. for 3 h. Additional amounts of potassium tert-butoxide (13.5 g) were added after 30 min. and 1 h, respectively. The mixture was poured into a saturated aqueous solution of ammonium chloride and the product was extracted into ethyl acetate. The combined organic phases were washed with a saturated aqueous solution of ammonium chloride and brine, dried over sodium sulfate and concentrated under reduced pressure. Column chromatography provided (7α)-7-ethenyl-3-methoxyestra-1,3,5(10),15-tetraen-17-one cyclic 1,2-ethanediyl acetal (17.54 g).

viii)—A solution of the product obtained in the previous step (31.47 g) in a mixture of acetone (507 ml) and water (43 ml) was treated with p-toluenesulfonic acid (1.48 g) and the reaction mixture was stirred at room temperature for 2 h. The reaction mixture was poured into a saturated aqueous solution of sodium hydrogencarbonate and the product was extracted into ethyl acetate. The combined organic phases were washed with brine, dried over sodium sulfate and concentrated under reduced pressure. Column chromatography afforded (7α)-7-ethenyl-3-methoxyestra-1,3,5(10),15-tetraen-17-one (23.92 g).

ix)—A solution of the product obtained in the previous step (23.9 g) in dry toluene (970 ml) was treated with p-toluenesulfonic acid (13.5 g) and heated under reflux for 15 min. After cooling, the reaction mixture was poured into a saturated aqueous solution of sodium hydrogencarbonate and the product was extracted into ethyl acetate. The combined organic phases were washed with brine, dried over sodium sulfate and concentrated under reduced pressure. Column chromatography afforded (7α)-7-ethenyl-3-methoxyestra-1,3,5(10),14-tetraen-17-one (14.9 g) and (7α,14β)-7-ethenyl-3-methoxyestra-1,3,5 (10), 15-tetraen-17-one (7.32 g).

x)—Sodium borohydride (1.47 g) was added to a solution of (7α)-7-ethenyl-3-methoxyestra-1,3,5(10),14-tetraen-17-one (1.50 g) obtained in the previous step in a mixture of tetrahydrofuran (27.8 ml), ethanol (27.8 ml) and water (4.55 ml). The reaction mixture was stirred for 50 min. and then poured into water. The product was extracted into ethyl acetate. The combined organic phases were washed with water and brine, dried over sodium sulfate and concentrated, to afford (7α,17β)-7-ethenyl-3-methoxyestra-1,3,5(10),14-tetraen-17-ol (1.47 g). The product was used in the following step without further purification.

xi)—A solution of the product obtained in the previous step (1.47 g) in dry tetrahydrofuran (26 ml) was added to refluxing liquid ammonia (105 ml). Lithium granulate (0.95 g) was added and the reaction mixture was stirred for 1.25 h. Dry tert-butanol (9.2 ml) was added and the reaction mixture was stirred for an additional 30 min. Solid ammonium chloride was added and the ammonia was allowed to evaporate. Water was added and the product was extracted into ethyl acetate. The combined organic phases were washed with a saturated aqueous solution of ammonium chloride and brine, dried over sodium sulfate, and concentrated under reduced pressure, to afford (7α,17β)-7-ethenyl-3-methoxyestra-2,5(10),14-trien-17-ol (1.48 g). The product was used in the following step without further purification.

xii)—Following a procedure analogous to that described under iii of Example 1, the product obtained in the previous step (1.48 g) was hydrolyzed to afford, after column chromatography and crystallization, (7α,17β)-7-ethenyl-17-hydroxyestra-4,14-dien-3-one (0.419 g), m.p. 129–136° C.

EXAMPLE 3

(7α,17β)-17-Hydroxy-7-propylestra-4,14-dien-3-one

The title compound was prepared in a manner analogous to that described under Example 1. $^1$H-NMR (CDCl$_3$) δ5.86 (bs, 1H), 5.08 (m, 1H), 4.00 (q, 1H, J=7.2 Hz), 1.00 (s, 3H), 0.89 (t, 3H, J=6.2 Hz).

EXAMPLE 4

(7α,17β)-17-Hydroxy-7-(2-propenyl)estra-4,14-dien-3-one i)—A mixture of lithium granulate (containing 0.5% sodium; 5.60 g) in dry diethyl ether (250 ml) was cooled to −30° C. 1-Bromo-3-[[(1,1-dimethylethyl) dimethylsilyl]oxy]propane (101.2 g) was added in 45 min. while maintaining the temperature below 0° C. After addition of the bromide, the reaction mixture was stirred for an additional 45 min. at 20° C. In a second flask, a suspension of copper(I) iodide (38.1 g) in dry tetrahydrofuran (200 ml) was cooled to −30° C. The solution of organolithium compound was added in 5 min. (−20≦T≦−10° C.), and stirring was continued for an additional 5 min. Then, a solution of (17α)-17-[(trimethylsilyl)oxy]-19-norpregna-4,6-dien-20-yn-3-one (Example 1, step i; 51.6 g) in dry tetrahydrofuran (200 ml) was added in 5 min. and the reaction mixture was stirred at −20° C. for 1 h. The mixture was poured into a saturated aqueous solution of ammonium chloride and concentrated ammonia (9:1) and the product was extracted into ethyl acetate. The combined organic phases were washed with a saturated aqueous solution of sodium hydrogencarbonate and brine, dried over sodium sulfate and concentrated. The residue was dissolved in acetone (500 ml). Hydrochloric acid (6 M, 25 ml) was added and the reaction mixture was stirred at room temperature for 2 h. A saturated aqueous solution of sodium hydrogencarbonate was added and the acetone was removed. The product was extracted into ethyl acetate; the combined organic phases were washed with brine, dried over sodium sulfate and concentrated. Column chromatography afforded (7α,17β)-17-hydroxy-7-(3-hydroxypropyl)-19-norpregn-4-en-20-yn-3-one (39.4 g).

ii)—A solution of the product obtained in the previous step (38.4 g) in a mixture of pyridine (215 ml) and acetic anhydride (108 ml) was stirred at room temperature for 1 h. The reaction mixture was poured into water (1000 ml) and stirring was continued for another 1 h. The product was extracted into ethyl acetate; the combined organic phases were washed with water and brine, dried over sodium sulfate and concentrated under reduced pressure, to give (7α,17α)-17-hydroxy-7-[3-(acetyloxy)propyl]-19-norpregn-4-en-20-yn-3-one (40.5 g). The product was used in the following step without further purification.

iii)—Following a procedure analogous to that described under iv of Example 1, the product obtained in the previous step (40.5 g) was converted to (7α)-7-[3-(acetyloxy)propyl]estr-4-ene-3,17-dione (39.0 g).

iv)—Following a procedure analogous to that described under v of Example 1, the product obtained in the previous step (39.0 g) was converted to (7α)-7-[3-(acetyloxy)propyl]-3-hydroxyestra-1,3,5(10)-trien-17-one (36.8 g).

v)—Following a procedure analogous to that described under vi of Example 1, the product obtained in the previous step (36.8 g) was converted to (7α)-7-[3-(acetyloxy)propyl]-3-methoxyestra-1,3,5(10)-trien-17-one (19.3 g).

vi)—Following a procedure analogous to that described under v of Example 2, the product obtained in the previous step (19.3 g) was converted (7α)-7-[3-(acetyloxy)propyl]-3-methoxyestra-1,3,5(10)-trien-17-one cyclic 1,2-ethanediyl acetal (21.8 g).

vii)—A solution of the product obtained in the previous step (21.8 g) in dry tetrahydrofuran (224 ml) was added dropwise to a suspension of lithium aluminium hydride (6.58 g) in dry tetrahydrofuran (448 ml), cooled to 0° C. After 1 h stirring, the reaction was quenched by addition of a saturated aqueous solution of sodium sulfate. Ethyl acetate was added, and the mixture was filtered over dicalite. The filtrate was concentrated under reduced pressure to give (7α)-7-(3-hydroxypropyl)-3-methoxyestra-1,3,5(10)-trien-17-one cyclic 1,2-ethanediyl acetal (18.9 g). The product was used in the following step without further purification.

viii)—A solution of the product obtained in the previous step (18.7 g) in dry dimethoxyethane (80 ml) was added dropwise to a solution of pyridinium tribromide (35.9 g) in a mixture of dry dimethoxyethane (80 ml) and ethylene glycol (28 ml) while avoiding the temperature to rise above room temperature. After 1 h stirring the mixture was poured into a solution of sodium thiosulfate (27.1 g) in water (159 ml) and the product was extracted into ethyl acetate. The combined organic phases were washed with water, a saturated aqueous solution of sodium hydrogencarbonate and brine, dried over sodium sulfate and concentrated under reduced pressure, to give (7α,16α)-16-bromo-7-(3-hydroxypropyl)-3-methoxyestra-1,3,5(10)-trien-17-one cyclic 1,2-ethanediyl acetal (24.3 g). The product was used in the following step without further purification.

ix)—Following a procedure analogous to that described under vii of Example 2, the product obtained in the previous step (24.3 g) was converted to (7α)-7-(3-hydroxypropyl)-3-methoxyestra-1,3,5(10),15-tetraen-17-one cyclic 1,2-ethanediyl acetal (13.1 g).

x)—Following a procedure analogous to that described under viii of Example 2, the product obtained in the previous step (5.46 g) was converted to (7α)-7-(3-hydroxypropyl)-3-methoxyestra-1,3,5(10),15-tetraen-17-one (5.01 g).

xi)—A solution of the ketone obtained in the previous step (3.19 g) and pyridinium p-toluenesulfonate (0.94 g) in isopropenyl acetate (94 ml) was heated under reflux for 1.5 h. After cooling, the reaction mixture was poured into a saturated aqueous solution of sodium hydrogencarbonate. The product was extracted into diethyl ether; the combined organic phases were washed with brine, dried over sodium sulfate, and concentrated under reduced pressure, to give (7α)-7-[3-(acetyloxy)propyl]-3-methoxyestra-1,3,5(10), 14,16-pentaen-17-ol acetate (3.69 g). The product was used in the following step without further purification.

xii)—Following a procedure analogous to that described under x of Example 2, the product obtained in the previous step (3.69 g) was converted to (7α,17β)-7-[3-(acetyloxy)propyl]-3-methoxyestra-1,3,5(10), 14-tetraen-17-ol (2.49 g).

xiii)—A solution of the alcohol obtained in the previous step (2.49 g) and imidazole (2.20 g) in dry dichloromethane (13 ml) was treated with tert-butyldimethylsilyl chloride (1.46 g). After 2 h stirring at room temperature the reaction mixture was poured into a saturated aqueous solution of sodium hydrogencarbonate. The product was extracted into diethyl ether; the combined organic phases were washed with water and brine, dried over sodium sulfate and concentrated under reduced pressure, to give (7α,17β)-7-[3-(acetyloxy)propyl]-17-[[(1,1-dimethylethyl)dimethylsilyl]oxy]-3-methoxyestra-1,3,5 (10), 14-tetraene (3.43 g). The product was used in the next step without further purification.

xiv)—Following a procedure analogous to that described under vii, the product obtained in the previous step (3.43 g) was converted to (7α,17β)-17-[[(1,1-dimethylethyl)dimethylsilyl]oxy]-7-(3-hydroxypropyl)-3-methoxyestra-1,3,5(10),14-tetraene (1.96 g).

xv)—Iodine (0.292 g) was added to a solution of triphenylphosphine (0.32 g) and imidazole (0.082 g) in dry dichloromethane (7.5 ml). After complete reaction of the iodine, a solution of the product obtained in the previous step (0.25 g) in dry dichloromethane (3 ml) was added and the mixture stirred for 30 min. at room temperature. Then it was poured into a saturated aqueous solution of sodium thiosulfate and the product extracted into diethyl ether. The combined organic phases were washed with water, a saturated aqueous solution of sodium hydrogencarbonate and brine, dried over sodium sulfate and concentrated under reduced pressure. Column chromatography afforded (7α,17β)-17-[[(1,1-dimethylethyl)dimethylsilyl]oxy]-7-(3-iodopropyl)-3-methoxyestra-1,3,5(10),14-tetraene (0.29 g).

xvi)—A solution of the iodide obtained in the previous step (0.17 g) in dimethylsulfoxide (5 ml) was treated with potassium tert-butoxide (1.62 g) and the reaction mixture was stirred at room temperature for 1 h. The mixture was poured into a saturated aqueous solution of ammonium chloride and the product was extracted into diethyl ether. The combined organic phases were washed with water and brine, dried over sodium sulfate and concentrated under reduced pressure. Column chromatography afforded (7α,17β)-3-methoxy-7-(2-propenyl) estra-1,3,5(10),14-tetraen-17-ol (0.075 g).

xvii)—The alcohol obtained in the previous step (0.15 g) in dry tetrahydrofuran (5 ml) was added to a refluxing solution of lithium (0.42 g) in liquid ammonia (30 ml). After 1 h stirring at −40° C., tert-butanol (4 ml) was added and stirring was continued for 30 min. Ethanol (8 ml) was added and the ammonia was allowed to evaporate. The mixture was poured into water and the product was extracted into ethyl acetate. The combined organic phases were washed with brine, dried over sodium sulfate and concentrated under reduced pressure, to give a mixture of (7α,17β)-3-methoxy-7-(2-propenyl)estra-2,5(10),14-trien-17-ol and (7α,17β)-3-methoxy-7-propylestra-2,5(10),14-trien-17-ol (0.144 g, ratio 2:3).

xviii)—Following a procedure analogous to that described under iii of Example 1, the product obtained in the previous step (0.144 g) was hydrolyzed to obtain, after column chromatography and preparative HPLC (reversed phase), (7α,17β)-17-hydroxy-7-(2-propenyl) estra-4,14-dien-3-one (0.018 g), $[\alpha]_D^{20}$=+6.2° (c=0.89, dioxane).

EXAMPLE 5

(7α,17β)-7-Butyl-17-hydroxyestra-4,14-dien-3-one (a) and (7α,17β)-7-(3-butenyl)-17-hydroxyestra-4,14-dien-3-one (b)

i)—Following a procedure analogous to that described under iv of Example 2, (7α,17β)-17-[[(1,1-dimethylethyl)dimethylsilyl]oxy]-7-(3-hydroxypropyl)-3-methoxyestra-1,3,5(10),14-tetraene(Example 4, step xiv; 0.40 g) was converted to 3-[(7α,17β)-17-[[(1,1-dimethylethyl)dimethylsilyl]oxy]-3-methoxyestra-1,3,5(10),14-tetraen-7-yl]propanal (0.40 g).

ii)—A mixture of methyltriphenylphosphonium bromide (0.94 g), potassium tert-butoxide (0.26 g) and dry toluene (10 ml) was heated under reflux for 1 h. A solution of the aldehyde obtained in the previous step (0.40 g) in dry toluene (5 ml) was added and heating was continued for another 1 h. After cooling, the reaction mixture was poured into a saturated aqueous solution of ammonium chloride. The product was extracted into ethyl acetate; the combined organic phases were washed with brine, dried over sodium sulfate and concentrated under reduced pressure. Column chromatography afforded (7α,17β)-7-(3-butenyl)-17-[[(1,1-dimethylethyl)dimethylsilyl]oxy]-3-methoxyestra-1,3,5(10),14-tetraene (0.40 g).

iii)—Following a procedure analogous to that described under iii of Example 1, the product obtained in the previous step (0.40 g) was converted to (7α,17β)-7-(3-butenyl)-3-methoxyestra-1,3,5(10),14-tetraen-17-ol (0.39 g).

iv)—Following a procedure analogous to that described under xvii of Example 4, the product described in the previous step (0.39 g) was converted to a mixture of (7α,17β)-7-butyl-3-methoxyestra-2,5(10),14-trien-17-ol and (7α,17β)-7-(3-butenyl)-3-methoxyestra-2,5(10),14-trien-17-ol (0.37 g, ratio 3:1).

v)—Following a procedure analogous to that described under iii of Example 1, the product obtained in the previous step (0.37 g) was hydrolyzed to give, after column chromatography and preparative HPLC (reversed phase), (7α,17β)-7-butyl-17-hydroxyestra-4,14-dien-3-one (0.043 g), $[\alpha]_D^{20}$=+7.6° (c=0.185, dioxane), and (7α,17β)-7-(3-butenyl)-17-hydroxyestra-4,14-dien-3-one (0.077 g), $[\alpha]_D^{20}$=+4.4° (c=0.475, dioxane).

EXAMPLE 6

(7α,17β)-7,13-Diethyl-17-hydroxygona-4,14-dien-3-one i)—Pyridinium-toluenesulfonate (5.0 g) was added to a solution of 13-ethylgon-4-ene-3,17-dione [Hoffmann-La Roche and Co.; AG, DE 1806410 (1967); 100.0 g] in a mixture of ethanol (600 ml), dioxane (800 ml) and triethyl orthoformate (199 ml). After 4.5 h stirring at room temperature pyridine (100 ml) was added and the reaction mixture was poured into a saturated aqueous solution of sodium hydrogencarbonate. The product was extracted into ethyl acetate; the combined organic phases were washed with water and brine, dried over magnesium sulfate and concentrated under reduced pressure, to give 3-ethoxy-13-ethylgona-3,5-dien-17-one (146.3 g). The product was used in the following step without further purification.

ii)—Following a procedure analogous to that described under vii of Example 4, the product obtained in the previous step (73.2 g) was converted to (17β)-3-ethoxy-13-ethylgona-3,5-dien-17-ol (58.0 g).

iii)—A solution of the product obtained in the previous step (58.0 g) in tetrahydrofuran (215 ml), containing pyridine (2.5 ml), was added to a suspension of tetrachloro-1,4-benzoquinone (49.6 g) in a mixture of ethanol (525 ml) and water (60 ml). The reaction mixture was stirred at room temperature for 4.5 h and then treated with a solution of sodium hydrogensulfite (26.7 g) in water (385 ml). After 30 min. stirring, a saturated aqueous solution of sodium sulfite was added and the product was extracted into ethyl acetate. The combined organic phases were washed with a saturated aqueous solution of sodium sulfite, water and brine, dried over magnesium sulfate and concentrated under reduced pressure, to give a brown oil (81.0 g). The reaction was repeated with 57.0 g of 3,5-diene to give 79.0 g of crude product. Column chromatography of the combined crude products afforded (17β)-13-ethyl-17-hydroxygona-4,6-dien-3-one (56.3 g).

iv)—Following a procedure analogous to that described under xiii of Example 4, the product obtained in the previous step (56.3 g) was converted to (17β)-17-[[(1,1-dimethylethyl) dimethylsilyl]oxy]-13-ethylgona-4,6-dien-3-one (65.6 g).

v)—Following a procedure analogous to that described under i of Example 2, using ethyl magnesium bromide, the product obtained in the previous step (25.0 g) was converted to (7α,17β)-7,13-diethyl-17-hydroxygon-4-en-3-one (8.13 g).

vi)—Following a procedure analogous to that described under iii of Example 2, the product obtained in the previous step (8.24 g) was converted to (7α,17β)-7,13-diethyl-3-methoxygona-1,3,5(10)-trien-17-ol (6.28 g).

vii)—Following a procedure analogous to that described under iv of Example 2, the product obtained in the previous step (5.72 g) was converted to (7α)-7,13-diethyl-3-methoxygona-1,3,5(10)-trien-17-one (5.61 g).

viii)—Following a procedure analogous to that described under v of Example 2, the product obtained in the previous step (5.61 g) was converted to (7α)-7,13-diethyl-3-methoxygona-1,3,5(10)-trien-17-one cyclic 1,2-ethanediyl acetal (6.99 g).

ix)—Following a procedure analogous to that described under vi of Example 2, the product obtained in the previous step (6.27 g) was converted to (7α,16β)-16-bromo-7,13-diethyl-3-methoxygona-1,3,5(10)-trien-17-one cyclic 1,2-ethanediyl acetal (8.47 g).

x)—Following a procedure analogous to that described under vii of Example 2, the product obtained in the previous step (8.47 g) was converted to (7α)-7,13-diethyl-3-methoxygona-1,3,5(10),15-tetraen-17-one cyclic 1,2-ethanediyl acetal (5.21 g).

xi)—A solution of the product obtained in the previous step (4.61 g) in dry toluene (120 ml) was treated with pyridinium p-toluenesulfonate (3.18 g) and heated under reflux for 1 h. After cooling, the reaction mixture was poured into a saturated aqueous solution of sodium hydrogencarbonate and the product was extracted into ethyl acetate. The combined organic phases were washed with water and brine, dried over magnesium sulfate and concentrated under reduced pressure, to give (7α)-7,13-diethyl-3-methoxygona-1,3,5(10),14-tetraen-17-one cyclic 1,2-ethanediyl acetal (4.44 g). The product was used in the following step without further purification.

xii)—A solution of the product obtained in the previous step (4.44 g) in dry toluene (120 ml) was treated with p-toluenesulfonic acid (2.29 g) and heated under reflux for 45 min. After cooling, the reaction mixture was poured into a saturated aqueous solution of sodium hydrogencarbonate and the product was extracted into ethyl acetate. The combined organic phases were washed with water and brine, dried over magnesium sulfate and concentrated under reduced pressure, to give (7α)-7,13-diethyl-3-methoxygona-1,3,5(10),14-tetraen-17-one (3.89 g). The product was used in the following step without further purification.

xiii)—Following a procedure analogous to that described under vii of Example 4, the product described in the previous step (3.89 g) was converted to (7α,17β)-7,13-diethyl-3-methoxygona-1,3,5(10),14-tetraen-17-ol (2.79 g).

xiv)—Following a procedure analogous to that described under xvii of Example 4, the product obtained in the previous step (2.0 g) was converted to (7α,17β)-7,13-diethyl-3-methoxygona-2,5(10),14-trien-17-ol (1.77 g).

xv)—Following a procedure analogous to that described under iii of Example 1, the product described in the previous step (1.77 g) was converted to (7α,17β)-7,13-diethyl-17-hydroxygona-4,14-dien-3-one (0.36 g), m.p. 181.5–183.5° C.

EXAMPLE 7

(7α,17β)-7-Ethenyl-13-ethyl-17-hydroxygona-4,14-dien-3-one i)—Following a procedure analogous to that described under i of Example 2, (17β)-17-[[(1,1-dimethylethyl)dimethylsilyl]oxy]-13-ethylgona-4,6-dien-3-one (Example 6, step iv; 25.0 g) was converted to (7α,17β)-7-ethenyl-13-ethyl-17-hydroxygon-4-en-3-one (8.20 g).

ii)—Following a procedure analogous to that described under iii of Example 2, the product obtained in the previous step (7.76 g) was converted to (7α,17β)-7-ethenyl-13-ethyl-3-methoxygona-1,3,5(10)-trien-17-ol (5.16 g).

iii)—Following a procedure analogous to that described under iv of Example 2, the product obtained in the previous step (5.43 g) was converted to (7α)-7-ethenyl-13-ethyl-3-methoxygona-1,3,5(10)-trien-17-one (5.08 g).

iv)—Following a procedure analogous to that described under v of Example 2, the product obtained in the previous step (4.92 g) was converted to (7α)-7-ethenyl-13-ethyl-3-methoxygona-1,3,5(10)-trien-17-one cyclic 1,2-ethanediyl acetal (5.42 g).

v)—Following a procedure analogous to that described under vi of Example 2, the product obtained in the previous step (5.08 g) was converted to (7α,16α)-16-bromo-7-ethenyl-13-ethyl-3-methoxygona-1,3,5(10)-trien-17-one cyclic 1,2-ethanediyl acetal (7.41 g).

vi)—Following a procedure analogous to that described under vii of Example 2, the product obtained in the previous step (7.41 g) was converted to (7α)-7-ethenyl-13-ethyl-3-methoxygona-1,3,5(10),15-tetraen-17-one cyclic 1,2-ethanediyl acetal (3.87 g).

vii)—Following a procedure analogous to that described under xi of Example 6, the product obtained in the previous step (3.42 g) was converted to (7α)-7-ethenyl-13-ethyl-3-methoxygona-1,3,5(10),14-tetraen-17-one cyclic 1,2-ethanediyl acetal (3.30 g).

viii)—Following a procedure analogous to that described under xii of Example 6, the product obtained in the previous step (3.30 g) was converted to (7α)-7-ethenyl-13-ethyl-3-methoxygona-1,3,5(10),14-tetraen-17-one (3.0 g).

ix)—Following a procedure analogous to that described under vii of Example 4, the product obtained in the previous step (3.00 g) was converted to (7α,17β)-7-ethenyl-13-ethyl-3-methoxygona-1,3,5(10),14-tetraen-17-ol (1.70 g).

x)—Following a procedure analogous to that described under xvii of Example 4, the product obtained in the previous step (1.49 g) was converted to (7α,17β)-7-ethenyl-13-ethyl-3-methoxygona-2,5(10),14-trien-17-ol (1.60 g).

xi)—Following a procedure analogous to that described under iii of Example 1, the product obtained in the previous step (1.60 g) was converted to (7α,17β)-7-ethenyl-13-ethyl-17-hydroxygona-4,14-dien-3-one (0.47 g), m.p. 141–145° C.

EXAMPLE 8

(3β,7α,17β)-7-Ethylestra-4,14-diene-3,17-diol

Following a procedure analogous to that described under vii of Example 4, the title compound was prepared from (7α,17β)-7-ethyl-17-hydroxyestra-4,14-dien-3-one (Example 1a). $^1$H-NMR (CDCl$_3$) δ5.39 (m, 1H), 5.01 (m, 1H), 4.21 (m, 1H), 3.96 (m, 1H), 0.98 (s, 3H), 0.87 (t, 3H, J=7.6 Hz).

EXAMPLE 9

(5α,7α,17β)-7-Ethyl-17-hydroxyestr-14-en-3-one

A solution of (7α,17β)-7-ethyl-17-hydroxyestra-4,14-dien-3-one (Example 1a; 0.67 g) in dry tetrahydrofuran (13 ml) was added to a refluxing solution of lithium (0.31 g) in liquid ammonia (44 ml). After 30 min. stirring at −40° C., solid ammonium chloride was added and the ammonia was allowed to evaporate. Water was added and the product was extracted into ethyl acetate. The combined organic phases were washed with a saturated aqueous solution of ammonium chloride and brine, dried over sodium sulfate and concentrated under reduced pressure. Column chromatography afforded (5α,7α,17β)-7-ethyl-17-hydroxyestr-14-en-3-one (0.21 g), $^1$H-NMR (CDCl$_3$) δ5.02 (s, 1H), 3.98 (t, 1H, J=8.4 Hz), 0.99 (s, 3H), 0.89 (t, 3H, J=7.5 Hz).

EXAMPLE 10
The LH Suppression Assay: Determination of Oral Activity

The in vivo potency (po) of several androgens of the invention was determined in a mature male castrated rat model, in comparison wih Segaloff compound. In this model serum LH is high (50× fold higher than with intact rats, due to the absence of the negative feedback of testicular testosterone). These rats are po treated for 4 days daily with a given compound of the invention in a suspension fluid of arachis oil. Before dosing and 3 hours after the last oral dose blood is collected via tail vene and in the serum LH is determined. Potency (po) of the androgens (ED$_{50}$) are expressed as the amount (mg/kg) of androgen which suppresses serum LH for 50% (±10%).

The rat LH Time-Resolved Immuno Fluorometric Assay (TR-IFMA) has been developed in house using home made reagents, a monoclonal catching antibody directed against the β-subunit of human chorion gonadotrophin (hCG, which cross react with rat β-subunit) and a biotin labelled detecting antibody (rabbit polyclonal antibody directed against the alfa-subunit of recombinant rat LH). Recombinant rat LH was prepared according to the methods described by Hakola et al (1997). In this two-site-IFMA, only intact rat LH is determined by a final incubation with streptavidin-europium. The detection in the IFMA is based on fluorescence of the lanthanide europium during a relative long exitation period. The concentration range of rat LH standard is 0.001–10 ng/ml, for optimal accuracy measurements of serum LH serum samples were diluted 8-times with assay buffer [Hakola, K., Boogaart, P. V., Mulders, J., de Leeuw, R., Schoonen, W., Heyst, J. V., Swolfs, A., Casteren, J. V., Huhtaniemi, I., and Kloosterboer, H. J., *Recombinant rat luteinizing hormone; production by Chinese hamster ovary cells, purification and functional characterization*, Molecular & Cellular Endocrinology 128, 47 (1997)].
Results

TABLE

ED$_{50}$ (po) of androgens of the invention required to suppress serum LH for 50% (±10%).

| Example | ED$_{50}$ (mg/kg) |
| --- | --- |
| 1a | 0.2 |
| 2 | 0.5 |
| Segaloff compound* | 5 |

*(7α,17β)-7-Methyl-17-hydroxyestra-4,14-dien-3-one

EXAMPLE 11
Determination of t$_{1/2}$ of Androgens of the Invention after Incubation with Human Hepatocytes The half-life of a compound as a result of contact with human hepatocytes holds as a reliable indication of metabolic stability. As it is well known that the absorption of this class of steroids is high, this assay provides an in vitro model for oral activity in humans. It will be understood that a shorter half-life indicates that a compound will be metabolized more rapidly or, vice versa, the longer the half-life, the better the compound may exert its effect upon the human body when administered orally.

Hepatocytes collected from healthy young (25–45 year) male organ donors were cryo preserved in liquid nitrogen and kept there until use. They were thawed at 37° C. in a waterbath, placed immediately on ice, washed twice in one volume of cold (4° C.) incubation medium [William's medium E (without phenol red) with Glutamax I®, gentamicin 50 μg/ml, insulin 1 μM, hydrocortisone hemisuccinate 10 μM, fetal calf serum 0% (v/v)], counted and the viability checked by Trypan blue exclusion. Cells were incubated as suspensions in 12-wells (non-coated) plates at a nominal density of 0.5×10$^6$ cells/well in 1.5 ml medium at 37° C. with an air/O$_2$/CO$_2$ mixture (55/40/5). The plates were set on an orbital shaker at approximately 10 rpm.

The hepatocytes were incubated with 10 nM final concentration of the compound to be tested. The incubations were stopped after 0.5, 1 and 3 h by pipetting the whole incubation mixture into a glass tube and adding one volume of acetone on ice. The acetone was dried under a nitrogen flow at room temperature, the volume adjusted to 1.5 ml and the tubes were centrifuged at 4° C. at 10.000×g for 30 min. The de-proteinized supernatants were collected for LC-MS/MS analysis.
Results

TABLE t$_{1/2}$ of androgens of the invention after incubation with human hepatocytes.

| Example | t$_{1/2}$ (min) |
| --- | --- |
| 1a | 157 |
| 2 | 40 |
| Segaloff compound* | 60 |

*(7α, 17β)-7-Methyl-17-hydroxyestra-4,14-dien-3-one

What is claimed is:

1. A kit for male contraception comprising a progestagen and an androgen, wherein the androgen is a pharmaceutical formulation comprising a compound of formula I:

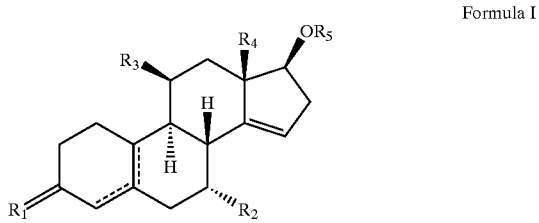

Formula I wherein
R$_1$ is O,(H,H), (H,OR), or NOR, with R being hydrogen. (C$_{1-6}$) alkyl or C$_{1-6}$) acyl;
R$_2$ is (C$_{2-4}$) alkyl, (C$_{2-4}$) alkenyl (C$_{2-4}$) alkynyl, cyclopropyl, or cyclopropenyl;
R$_3$ is hydrogen, (C$_{1-2}$) alkyl, or ethenyl;
R$_4$ (C$_{1-2}$) alkyl; and,
R$_5$ is hydrogen or (C$_{1-15}$) acyl.

2. The kit according to claim 1, wherein R$_2$ is selected from the group consisting of ethyl, ethenyl, ethnyl, propyl, 1-propenyl, 2-propenyl, 1-propynyl, 1,2-propadienyl and cyclpropyl.

3. The kit according to claim 2, where R2 is selected from the group consisting of aethyl, a ethenyl and a ethynyl.

* * * * *